(12) United States Patent
Cheng et al.

(10) Patent No.: US 11,119,048 B2
(45) Date of Patent: Sep. 14, 2021

(54) CHEMILUMINESCENCE DETECTION EQUIPMENT AND ITS OPERATION METHOD

(71) Applicant: Shaoxing PushKang Biotechnology Co., LTD., Shaoxing (CN)

(72) Inventors: Lin Cheng, Shaoxing (CN); Chun-Yan Liu, Shaoxing (CN); Ya-Xiong Zhang, Shaoxing (CN); Xi-Jiang Qian, Shaoxing (CN); Quan-Qi Yang, Shaoxing (CN); Xian-Hua Wang, Shaoxing (CN); Hui Xu, Shaoxing (CN); Bo Yu, Shaoxing (CN); Ye-Qi Jin, Shaoxing (CN)

(73) Assignee: SHAOXING PUSHKANG BIOTECHNOLOGY CO., LTD., Shaoxing (CN)

( * ) Notice: Subject to any disclaimer, the term of this patent is extended or adjusted under 35 U.S.C. 154(b) by 333 days.

(21) Appl. No.: 16/214,023

(22) Filed: Dec. 7, 2018

(65) Prior Publication Data

US 2020/0096449 A1    Mar. 26, 2020

(30) Foreign Application Priority Data

Sep. 25, 2018    (CN) .............................. 201811115377

(51) Int. Cl.
*G01N 1/00* (2006.01)
*G01N 21/76* (2006.01)
*B01L 9/00* (2006.01)
*G01N 33/53* (2006.01)

(52) U.S. Cl.
CPC .............. *G01N 21/76* (2013.01); *B01L 9/523* (2013.01); *G01N 33/53* (2013.01)

(58) Field of Classification Search
None
See application file for complete search history.

(56) References Cited

U.S. PATENT DOCUMENTS

| 5,270,211 | A | * | 12/1993 | Kelln | G01N 35/0092 422/547 |
| 5,788,928 | A | | 8/1998 | Carey et al. | |
| 2015/0233751 | A1 | | 8/2015 | Blake et al. | |
| 2017/0089934 | A1 | | 3/2017 | Hori et al. | |

FOREIGN PATENT DOCUMENTS

CN    107843737 A    3/2018

* cited by examiner

*Primary Examiner* — Jyoti Nagpaul
(74) *Attorney, Agent, or Firm* — Cheng-Ju Chiang (57) ABSTRACT

A highly integrated, fully automatic chemiluminescence detection equipment and its operation method are disclosed. The chemiluminescence detection equipment comprises a control module, a first electrical machine, a reagent wheel disc tank, a sampling module, a washing module, a second electrical machine and a detection module. Compared with the traditional large-scale chemiluminescence detection equipment, the chemiluminescence detection equipment of the present invention has the advantage of high integration, and greatly reduces the overall volume and weight of the chemiluminescence detection equipment.

13 Claims, 11 Drawing Sheets

CHEMILUMINESCENCE DETECTION EQUIPMENT AND ITS OPERATION METHOD

TECHNICAL FIELD

The present invention relates to a chemiluminescence detection, particularly, to a highly integrated chemiluminescence detection equipment and its operation method.

BACKGROUND OF RELATED ARTS

With the rapid development of science and technology, the behaviors and processes of all medical detection are gradually towards modularization and automation. At present, for the automatic process of tube luminescence detection, the sample, magnetic beads antibodies and enzyme-labeled antibodies are mixed and incubated in the detection tube, and then the magnetic beads were adsorbed on the wall of the tube by magnet(s) and the mixture liquid is sucked away.

The magnet field is removed, and washing buffer is poured to mix the magnetic beads. Then, the magnetic beads are adsorbed on the wall of the tube by the magnet(s) and the liquid is sucked away. After repeating the above steps twice, the magnet field is removed, and a substrate is added to mix the liquid for performing a detection of luminescence detection.

At present, the main domestic large-scale tubular luminescent instrument is characterized by all the steps of chemiluminescence analyzed into module operation, including mechanical arm grabbing reaction cup, mixing, incubation, washing, reaction, detection and other steps completed by each of the corresponding modules. For example, the existing large-scale luminescent instrument has large volume and weight, high cost and large sample throughput. For small private community hospitals, the sample size of township hospitals is small, and the economic power is insufficient, so the large-scale luminescent instrument is obviously not practical. For example, in Raytheon's large-scale automatic luminescent immunoassay instrument, in order to complete the above steps of chemiluminescence detection, modular equipment can be used to complete these steps. That is to say, after completing one step, the next module is followed to perform the next detection. However, the number of sampling pins and sampling arms increased greatly. In addition, multiple different modules set up separately will greatly increase the size of the entire equipment, and the corresponding cost will be greatly increased.

In addition, reagent dosage of the existing tubular chemiluminescence is relatively large. For the higher cost of reagents, it can significantly reduce user's detection cost of chemiluminescence by reducing the reagent dosage. Especially, for the basic medical institutions, they need miniaturized, simple detection equipment.

Chemiluminescence immunoassay disc based on microfluidic technology has the advantages of small size, lower price and no waste liquid exhaust such that it plays an important role in environmental protection and user safety. In addition, there is a centrifugal magnetic particle manipulation and detection device and its operation method in the prior art, which describes a method of manipulating magnetic particles based on centrifugal microfluidic disc. This method has a great value for the study of integrated chemiluminescence detection, and the chemiluminescence detection equipment with simplified structure can be obtained based-on such method.

For the basic medical institutions, there are fewer samples per day, and they do not need bulky expensive equipment. They need to meet the current dosage and the local medical level. Therefore, a chemiluminescence detection equipment with simple operation is urgently needed.

SUMMARY

To resolve the drawbacks of the prior arts, the present invention discloses a chemiluminescence detection equipment comprising a control module, a first electrical machine, a reagent wheel disc tank, a sampling module, a washing module, a second electrical machine and a detection module.

The first electrical machine is connected to the control module. The reagent wheel disc tank is connected to the first electrical machine. The sampling module is connected to the control module, wherein the sampling module includes a sampling pin.

The washing module is connected to the sampling module and the control module to clean the sampling pin. The second electrical machine is connected to the control module, and the detection module including a detection rotatable module, a heating device, a light detection device and a light tight cover.

The detection rotatable module is connected to the second electrical machine, and the heating device is connected to the control module and the detection rotatable module. The light detection device is connected to the control module and the detection rotatable module, and the light tight cover is used to cover the detection rotatable module. The light-tight cover is provided with at least one light-tight hole, wherein each light-tight hole is opened and closed by an electromagnetic valve, and the electromagnetic valve is connected with the control module.

Embodiments of the invention are illustrated by way of example, and not by way of limitation, in the figures of the accompanying drawings in which like reference numerals refer to similar elements:

BRIEF DESCRIPTION OF THE DRAWINGS

To clearly illustrate the embodiments of the present invention, a brief description of the accompanying drawings to be used in the embodiments will be given below. Obviously, the accompanying drawings described below are only some of the embodiments of the present invention and, for those of ordinary skill in the art, other drawings can be obtained according to the structure shown in the drawings.

The implementations, functional characteristics and advantages of the present invention will be further illustrated with reference to the drawings in combination with the embodiments.

DETAILED DESCRIPTION OF THE INVENTION

In order to understand the technical features and practical efficacy of the present invention and to implement it in accordance with the contents of the specification, hereinafter, preferred embodiments of the present invention will be described in detail with reference to the accompanying drawings.

It should be noted that all directional indications (such as upper, lower, left, right, front, rear, etc.) in some embodiments of the present invention are only used to explain the relative position relationship, motion conditions, etc. between the components in a particular condition (as shown in the drawings). If the particular condition changes, the directional indication changes accordingly.

In the present invention, the terms "connection" and "fixation" should be understood in a broad interpretation unless otherwise specified and defined. For example, "fixation" may be a fixed connection, a detachable connection, or an integral whole; "connection" may be a mechanical connection, or an electrical connection; it may be a direct connection, or it may be indirectly connected through an intermedia; and can be connected within two components or the interaction between two components unless otherwise specified. For those of ordinary skill in the art, the specific meaning of the above-mentioned terms in the present invention can be understood according to specific cases.

In addition, descriptions relating to "first" and "second" in the present invention are used only for descriptive purposes and are not understood to indicate or imply their relative importance or to imply the number of the indicated technical features. Thus, the features defined as "first" and "second" may explicitly or implicitly include at least one of the features. In addition, the technical schemes among the various embodiments may be integrated with each other, but must be achieved based on the ability of a person of ordinary skill in the art. When the combination of technical schemes is inconsistent or impossible to achieve, it should be considered that the combination of such technical schemes does not exist, nor is it within the claim scape of the invention.

Figure 1:
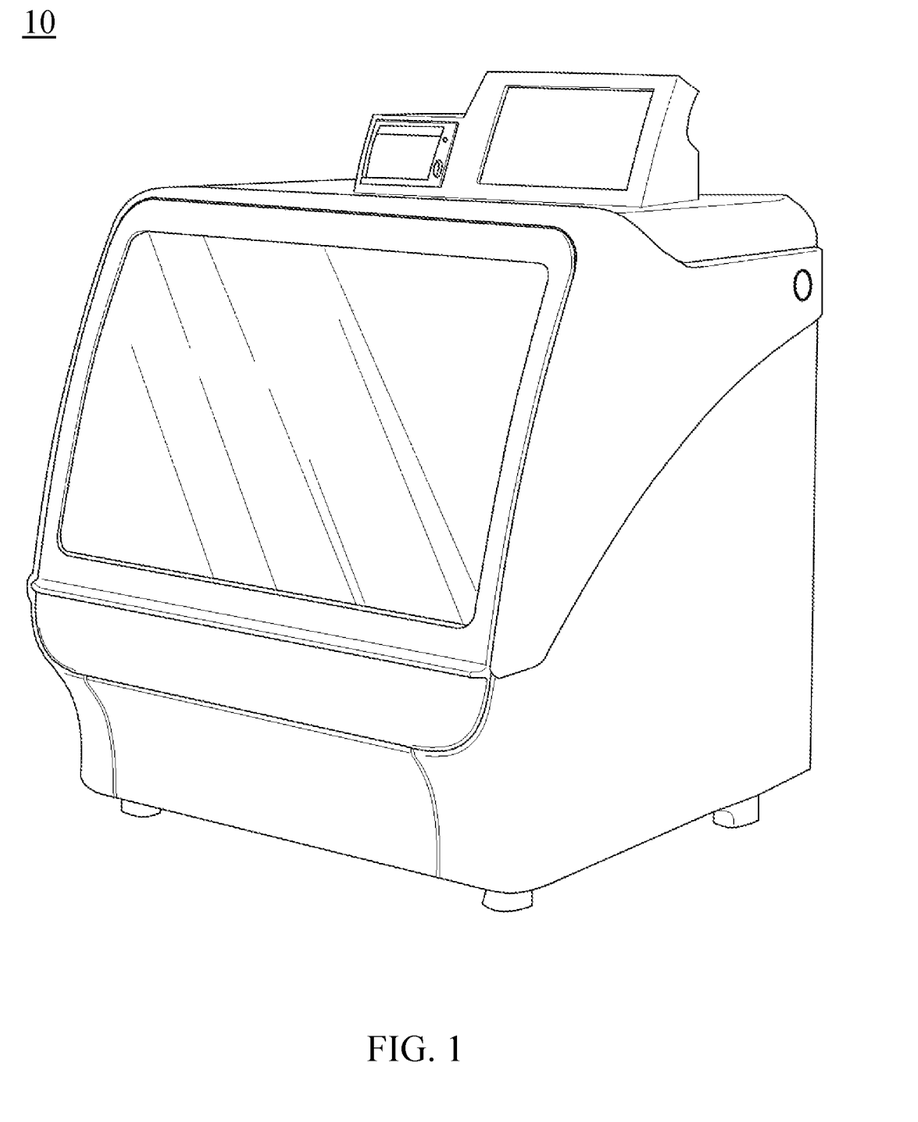
FIG. 1 is a schematic diagram of the appearance structure of an embodiment of the present invention.
Figure 2:
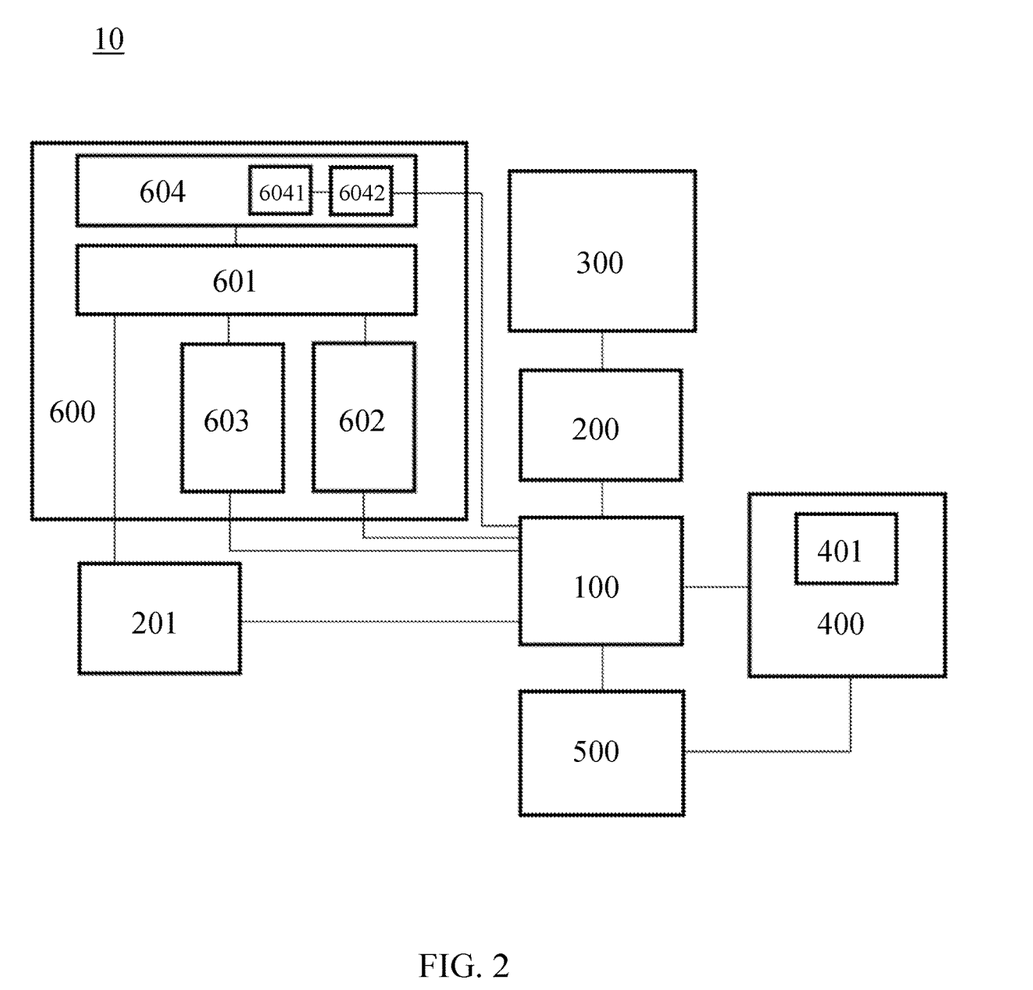
FIG. 2 is a system architecture diagram in accordance with one embodiment of the present invention.

Referring now to FIG. 1 and FIG. 2, FIG. 1 shows a schematic diagram of the appearance structure in accordance with one embodiment of the present invention, and FIG. 1 shows a system architecture diagram in accordance with one embodiment of the present invention. As shown in FIG. 1 and FIG. 2, the chemiluminescence detection equipment 10 illustrated in an embodiment of the present invention comprises a control module 100, a first electrical machine 200, a reagent wheel disc tank (cabin) 300, a sampling module 400, a washing module 500, a second electrical machine 201 and a detection module 600.

The first electrical machine 200 is connected to the control module 100. The reagent wheel disc tank 300 is connected to the first electrical machine 200. The sampling module 400 is connected to the control module 100. The sampling module 400 includes a sampling pin 401.

The washing module 500 is connected to the sampling module 400 and the control module 100. The washing module 500 is use to clean the sampling pins 401. The second electrical machine 201 is connected to the control module 100. The detection module 600 includes a detection rotatable module 601, a heating device 602, a light detection device 603 and a light tight cover 604.

The detection rotatable module 601 is connected to the second electrical machine 201. The heating device 602 is connected to the control module 100 and the detection rotatable module 601. The light detection device 603 is connected to the control module 100 and the detection rotatable module 601. The light tight cover 604 may be operated (opened and closed) to cover the detection rotatable module 601. The light-tight cover 604 is further provided with at least one light-tight hole 6041, wherein each light-tight hole 6041 is opened and closed by an electromagnetic valve 6042, and the electromagnetic valve 6042 is connected with the control module 100.

Figure 3:
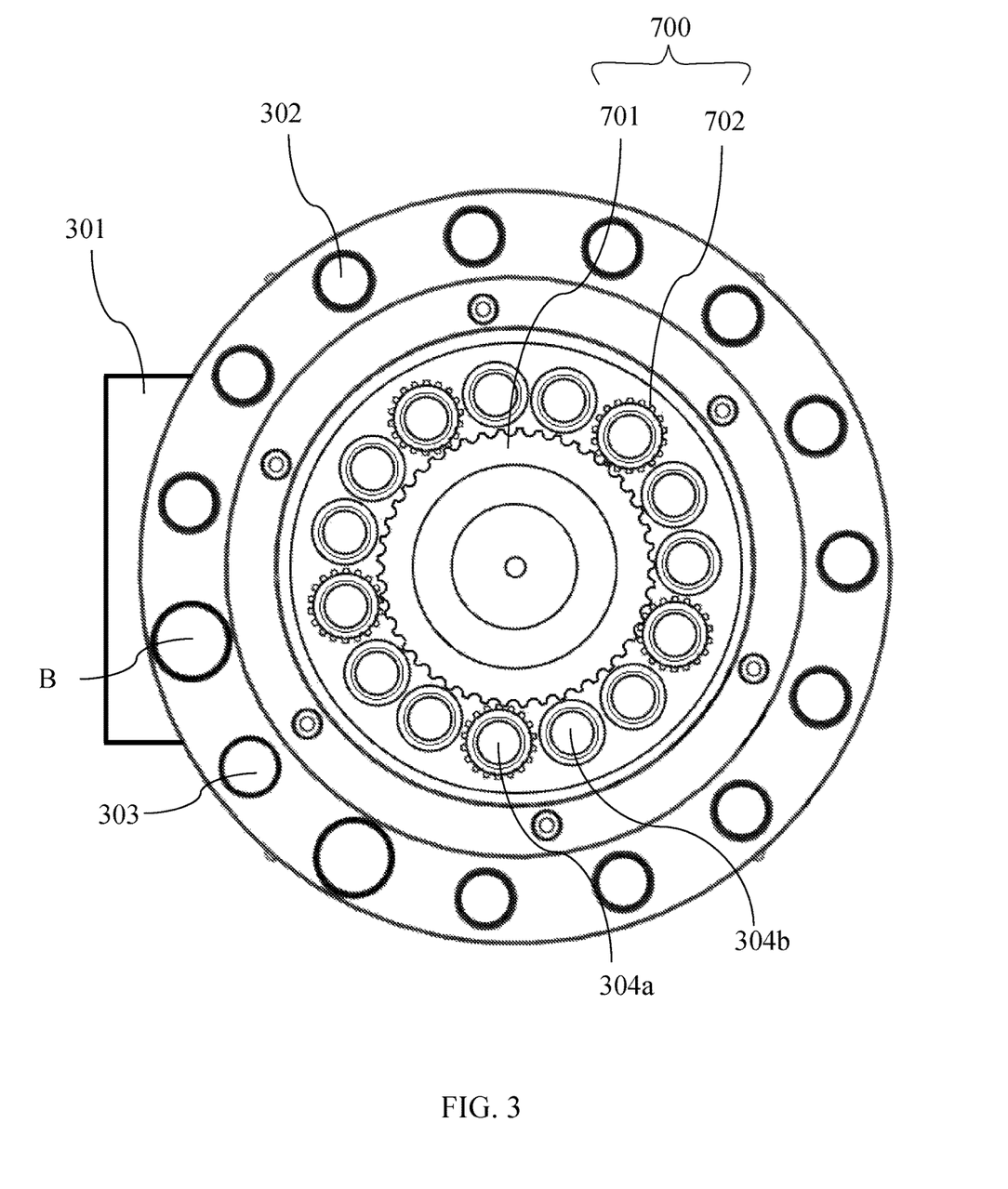
FIG. 3 is a schematic diagram of the reagent wheel disc tank of one embodiment of the invention.

According to the appearance of FIG. 1 and the system architecture of FIG. 2, the embodiment of the invention integrates a plurality of modules into a miniature automatic machine, which can meet the requirements of miniature medical detection and greatly reduce the cost of reagents. In this embodiment, referring to FIG. 3, FIG. 3 is a schematic diagram of the reagent wheel disc tank of one embodiment of the invention. The embodiment of the present invention of FIG. 3 shows that the reagents and samples are centralized and systemized to achieve effective management. As shown in FIG. 3, the reagent wheel disc tank 300 of the present embodiment includes a cooling device 301, which is arranged on the bottom of the reagent wheel disc tank 300. In this embodiment, the cooling device 301 is a Peltier cooler, more particularly using a Peltier cooler produced by Peltier Semiconductor Ltd (China).

There are a plurality of sample storage slots (grooves) 302, a substrate storage slot 303 and a plurality of reagent storage slots 304a and 304b are configured within the reagent wheel disc tank 300. Among them, the plurality of sample storage slots 302 are arranged on the outer ring of the reagent wheel disc tank 300. The substrate storage slot 303 is also arranged on the outer ring of the reagent wheel disc tank 300. The reagent storage slots 304a and 304b are arranged on the inner ring of the reagent wheel disc tank 300. In addition, in order to prevent technicians from confusing samples and substrates, identifiers (identification objects or marks) B with different colors, sizes and/or shapes are arranged on both sides of the substrate storage slot 303. The reagent storage slots 304a and the reagent storage slots 304b are arranged by a concentric circle, while the substrate storage slot 303, the identifiers B and the sample storage slots 302 are arranged by a concentric circle.

In this embodiment, the difference between the reagent storage slot 304a and the reagent storage slot 304b is whether reagent liquid filled in the slot needs to be uniformly mixed. For example, a common stationary phase reagent-magnetic bead, the reagent with magnetic bead before extracting must be uniformly mixed with the liquid without precipitation. Therefore, the first electrical machine 200 of the present embodiment actually engages with the reagent wheel disc tank 300 through a gear set 700. More particularly, the gear set 700 includes a first gear 701 connected to the first electrical machine 200, and a plurality of second gears 702 connected to the reagent storage slots 304a. Each of the plurality of second gears 702 can be configured on the bottom of the corresponding reagent storage slots 304a. The first gear 701 is driven to rotate by the first electrical machine 200 and the second gears 702 is then rotating followed with the first gear 701. The reagent storage slots 304a can be rotated together with the second gears 702. In this way, the magnetic beads filled in the reagent storage slots 304a can easily maintain uniformly mixing.

Figure 4:
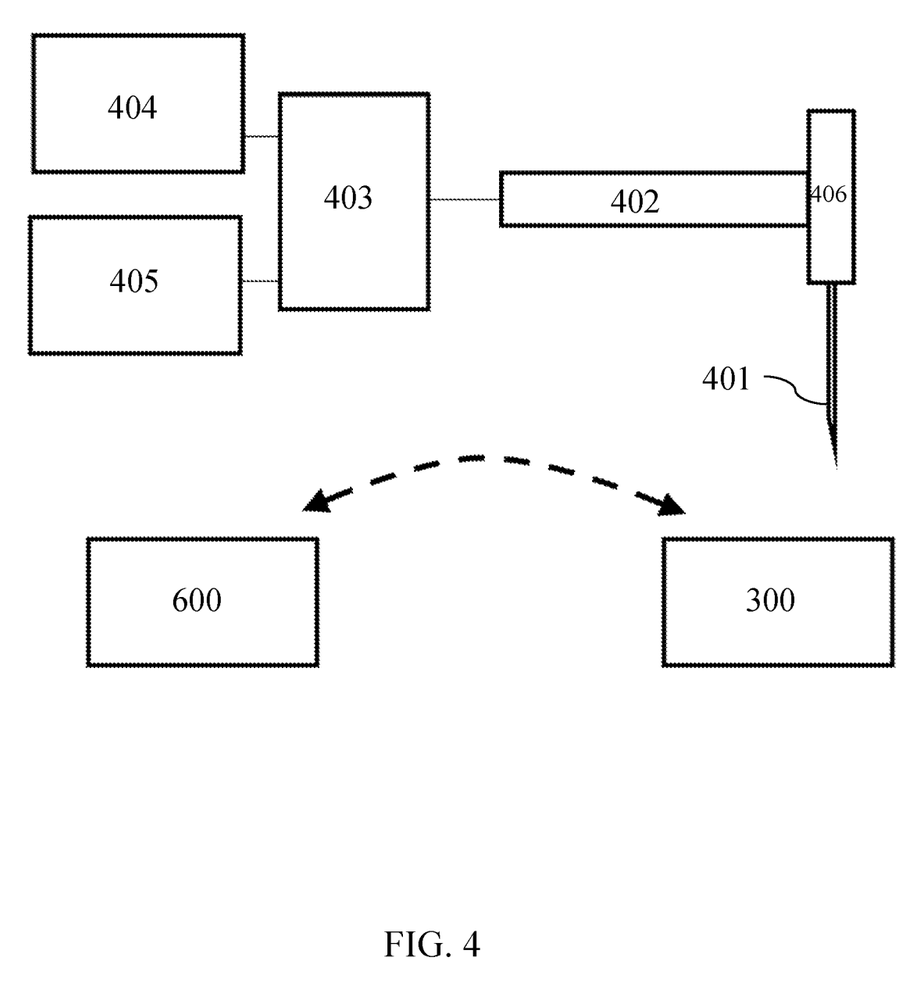
FIG. 4 illustrates the system architecture diagram of the sampling module of one embodiment of the invention.

Next, refer to FIG. 4, FIG. 4 illustrates the system architecture diagram of the sampling module of one embodiment of the invention. As shown in FIG. 4, the sampling module 400 of this embodiment of the present invention comprises a sampling arm 402, a driving component 403, a third electrical machine 404, and a fourth electrical machine 405. The sampling arm 402 is connected to the sampling pin 401. For example, the sampling pin 401 is connected to a resistance sensor 406 on the sample arm 402. The driving component 403 is connected to the sampling arm 402. The third electrical machine 404 and the fourth electrical machine 405 are connected to the driving component 403, respectively. The third electrical machine 404 controls a transverse movement of the sampling arm 402, and the fourth electrical machine 405 controls a longitudinal movement of the sampling arm 402, wherein the transverse movement and the longitudinal movement are in an identical plane.

In other words, by co-operating of the driving component 403, the third electrical machine 404 and the fourth electrical machine 405, the sampling pin 401 can be freely moved between the reagent wheel disc tank 300 and the detection module 600, indicating by the two-way dotted arrow in FIG. 4. With the upward and downward movement of the sampling pin 401, all the samples or reagents of the detection module 600 can be filled by a single sampling pin 401. When the sampling pin 401 moves up and down, the resistance sensor 406 can be used to detect whether the sampling pin 401 is entering into the liquid level of the reagent. The contact condition and depth of the sampling pin 401 with the reagent can be known by sensing the resistance or current change of the sampling pin 406.

In addition, the washing module 500 of this embodiment can highly washing the sampling pin 401. The way of washing can be performed by carbon dioxide, pure water or ultrasonic vibration. Therefore, after reagent or sample is fully filled by the sampling pin 401, it can be reused as washing by the washing module 500. The number of the sampling arm 402 and the sampling pin 401 are greatly reduced, and volume of the chemiluminescence detection equipment 10 is greatly simplified.

Figure 5:
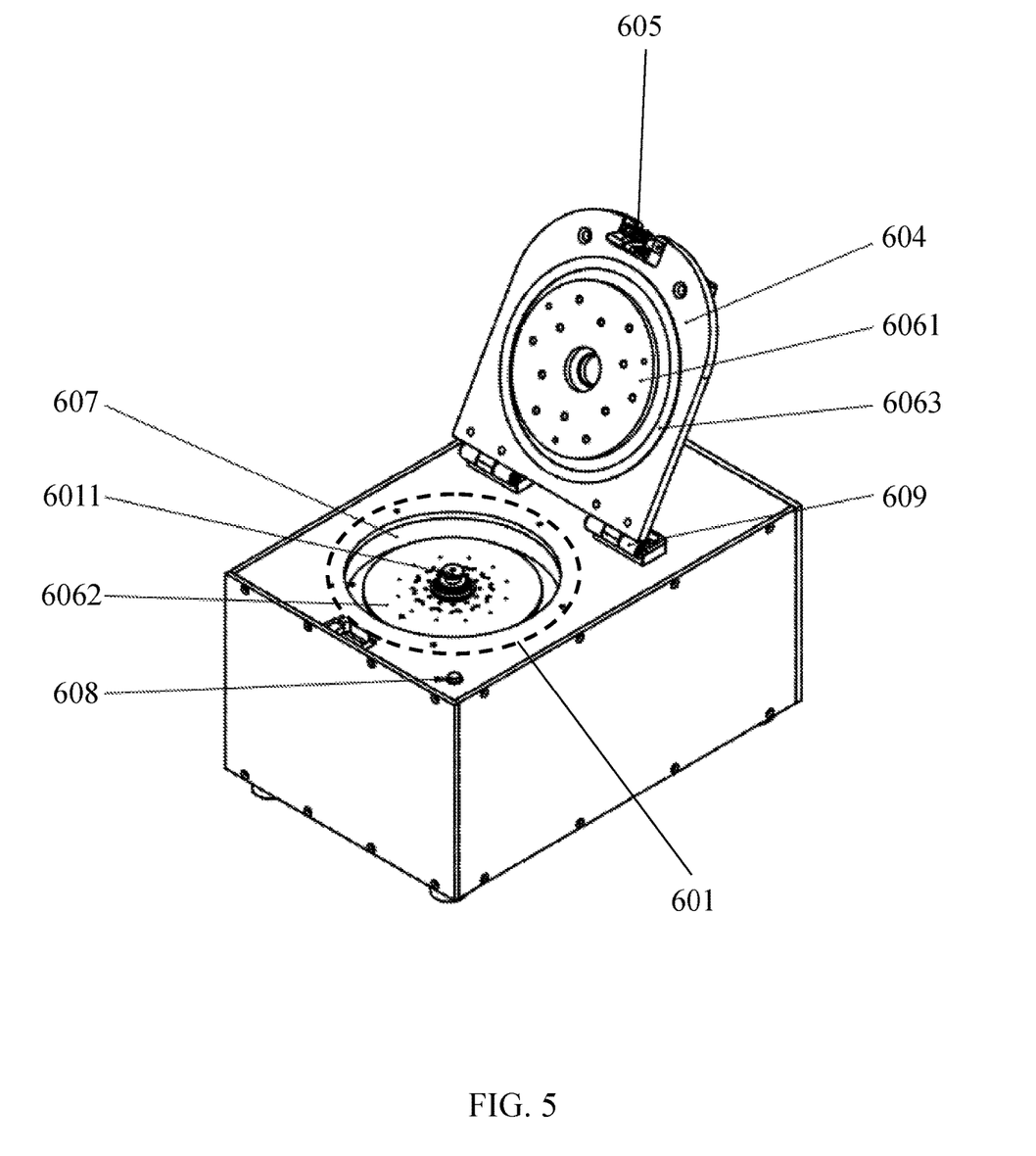
FIG. 5 illustrates a schematic diagram of the appearance structure of the detection module of one embodiment of the invention.
Figure 6:
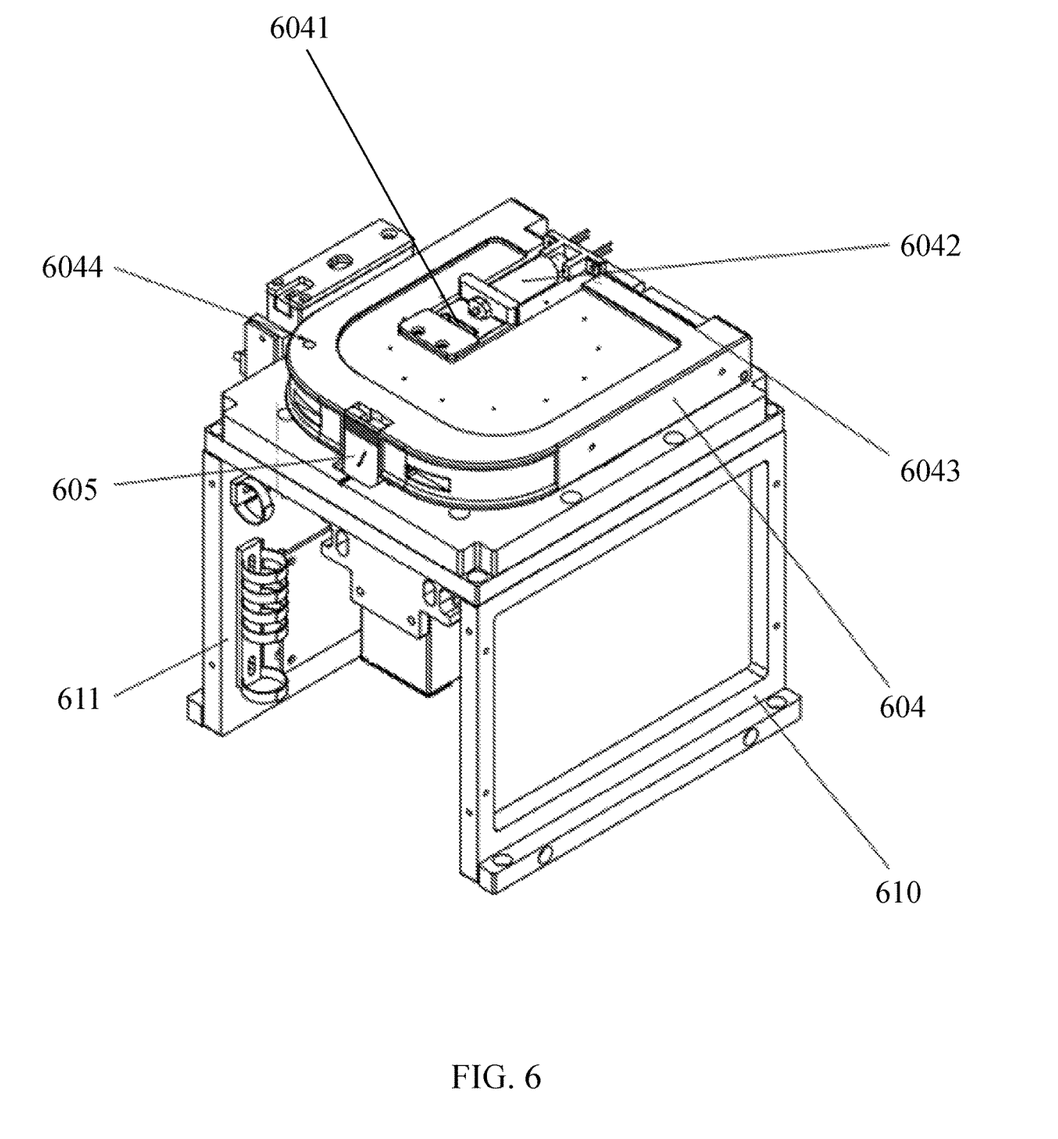
FIG. 6 illustrates a schematic diagram of the internal structure of the detection module of one embodiment of the invention.

Referring to FIG. 5 and FIG. 6, FIG. 5 shows a schematic diagram of the appearance structure of the detection module of this embodiment of the invention, and FIG. 6 shows a schematic diagram of the internal structure of the detection module of this embodiment of the invention. As can be seen from the diagrams of FIG. 5 and FIG. 6, the internal structure of the detection module 600 mainly includes a main frame 610 as a support to set up the detection rotatable module 601. On the main frame 610 below the detection rotatable module 601, a setting frame 611 is arranged for the light detection device 603.

As shown in FIG. 5 and FIG. 6, the light-tight cover 604 of the detection module 600 is provided with a lock fastener 605 so that the light-tight can be maintained during the operation of the detection without being affected by the environmental light. In fact, when the sampling operation is performed in this embodiment, the opening and closing of the light-tight hole 6041 is controlled by the solenoid valve 6042, and the effect of accurate sampling is achieved by simultaneously operably rotating the detection rotatable module 601. A detection disc D, under-sampling and under-detection, is arranged in the detection rotatable module 601.

Furthermore, the detection rotatable module 601 in this embodiment is provided with a fastener 6011 to control the tightness of the connection with the detection disc D. The connection structure between the fastener 6011 and the detection disc D may be not limited to a circular shape with a notch (refer to the central part D3 in FIG. 10). The substantial structure of the detection rotatable module 601 can be illustrated with reference to the schematic diagram of FIG. 7, which is a detecting schematic diagram of the detection module according to the embodiment of the present invention.

Figure 7:
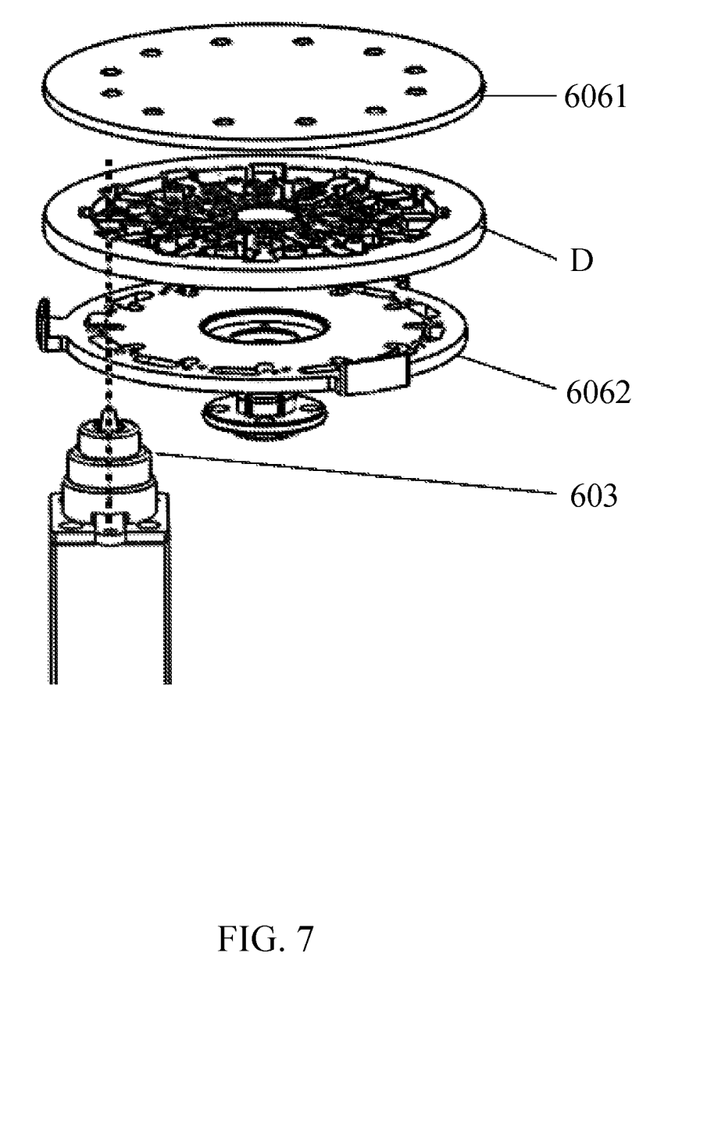
FIG. 7 illustrates a detecting schematic diagram of the detection module according to one embodiment of the present invention.

As shown in FIG. 7, it is evidently that the detection disc D is enclosed by the upper magnetic cover 6061 and the lower magnetic base 6062, and then the detection operation is performed along the direction of the dotted line in FIG. 7 by the light detection device 603. In other words, the upper magnetic cover 6061 and the lower magnetic base 6062 are configured as shown in FIG. 5. The upper magnetic cover 6061 is arranged on the light-tight cover 604, and the upper magnetic cover 6061 has a first light-tight member 6063 on the periphery of the upper magnetic cover 6061 to further prevent from ambient light interference. In this embodiment, the upper magnetic cover 6061 is used for uniformly mixing the magnetic beads in the chemiluminescent immunoreaction. The detection disc D can be essentially a centrifugal microfluidic control disc. The centrifugal microfluidic control disc provides a reaction environment for the chemiluminescence reaction to complete the whole process of the chemiluminescence reaction.

As for the lower magnetic base 6062, it is set in the detection rotatable module 601. The lower magnetic base 6062 is mainly used to load (support) the detection disc D and capture or release magnetic beads in chemiluminescent immunoreaction. Further, air bath or water bath is needed to control the reaction temperature during detection process such that the detection rotatable module 601 includes a heat bath 607 to provide the necessary temperature-controlled reaction conditions. A limit pivot 609 connected with the light-tight cover 604 can restrict opening and closing action and pivot angle of the light-tight cover 604 to avoid damaging its components and structure due to improper closure. As for the power indicator 608 installed on the outer shell of the detection module 600, it can show whether the detection module 600 is in operation or not, so as to avoid the consequence of detection failure caused by a technician opening the light-tight cover 604 as the detection is in operation.

In addition, as shown in FIG. 6, the solenoid valve 6042 is electrically connected to a first sensor 6043, and the light-tight cover 604 is electrically connected to a second sensor 6044. In this embodiment, the first sensor 6043 is mainly used to confirm the position of the solenoid valve 6042 to confirm the operation of opening or closing the light-tight hole 6041 to avoid error of operation. As for the second sensor 6044, it is used to confirm whether the light-tight cover 604 is substantially covered to facilitate the detection.

From the illustration of FIGS. 5-7, they can be seen that the detection module 600 mainly includes the detection rotatable module 601 and the light detection device 603 for co-operating of detection. In this embodiment, the heating device 602 is connected with the detection rotatable module 601. As the turntable module 601 includes the heat bath 607, the heating device 602 may be a heating tube or other device to facilitate incubating. Further, referring to FIG. 8, it shows a cross-sectional view of a structure of the detection rotatable module of this embodiment of the present invention.

Figure 8:
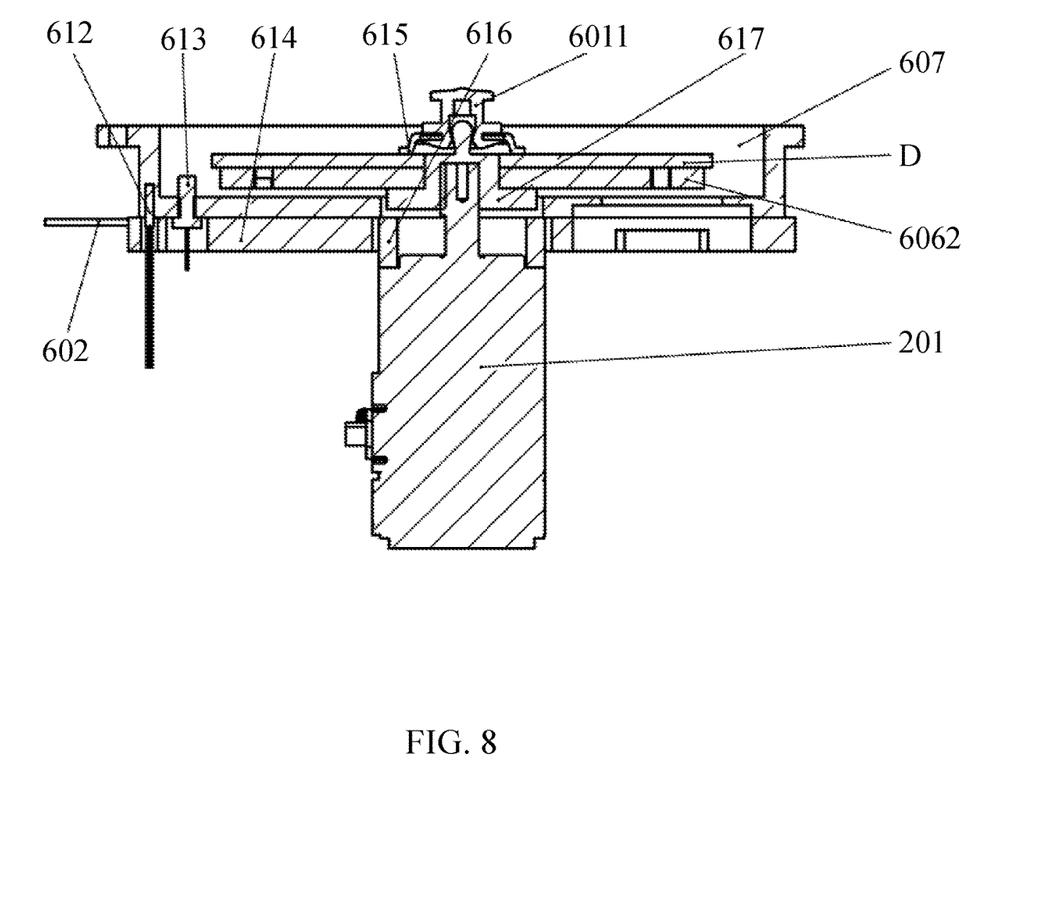
FIG. 8 illustrates a cross-sectional view of a structure of the detection rotatable module of one embodiment of the present invention.

As shown in FIG. 8, it illustrates the structure of the detection rotatable module 601 of this embodiment. The detection rotatable module 601 is rotated by a buffer block 616 and a fixed rotor 617 connected to the second electrical machine 201. The heating device 602 is arranged on one side of the detection module to generate a required temperature of incubation reaction in the heat bath 607. In this embodiment, the buffer block 616 is arranged on the second electrical machine 201 to avoid vertical motion or vibration relative to ground level caused by the operation of the second electrical machine 201.

As for the fixed rotor 617, it is spaced above the buffer block 616 and passed through the heat bath 607. The rotation power of the second electrical machine 201 can be outputted through the fixed rotor 617. The two sides of the buffer block 616 can be provided with an insulating element 614, which is arranged below the heat bath 607 to avoid damaging to lower machine parts caused by conductive temperature from of the heat bath 607, in addition, to further maintain the required incubation temperature in the heat bath 607 to avoid temperature loss affected by environmental temperature.

In this embodiment, a first temperature sensor 612 and a second temperature sensor 613 may be configured on the heat bath 607. The first temperature sensor 612 is embedded in the inner wall of the heat bath 607 to detect temperature change of the heat bath 607. In this embodiment, the heat bath 607 is not limited to be made by metal material with a cavity. In order to avoid overheating, the second temperature sensor 613 is configured to pass through the heat bath 607, and directly contacts the environment in the heat bath 607 to detect the temperature changes of gas or liquid in the cavity of the heat bath 607. In some embodiments, the number of the first temperature sensor 612 and the second temperature sensor 613 is not limited to one, and which should be set on some components needed to monitor temperature changes.

The lower magnetic base 6062 is installed on the fixed rotor 617 to receive the rotating power of the second electrical machine 201 so that the detection disc D mounted on the lower magnetic base 6062 is driven to rotate together. In order to fix the detection disc D, a pressing cover 615 can be arranged between the fastener 6011 and the detection disc D. The fastener 6011 is operably locking or loosening the detection disc D while pressing the detection disc D by the pressing cover 615 to ensure the safety of rotating detection.

Figure 9:
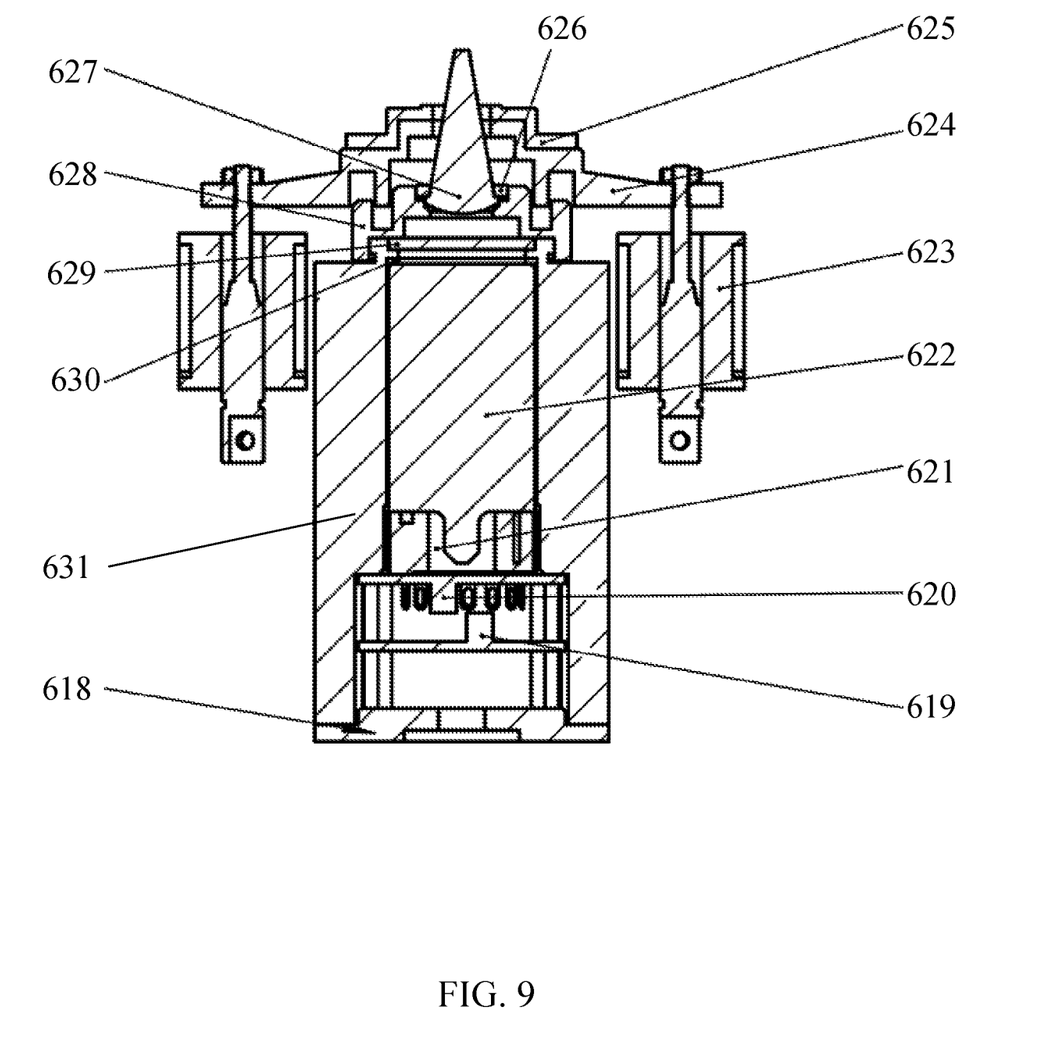
FIG. 9 illustrates a structural profile of the light detection device of one embodiment of the invention.

Next, referring to FIG. 9, it illustrates a structural profile of the light detection device of one embodiment of the invention. As shown in FIG. 9, the light detection device 603 in this embodiment mainly comprises a photomultiplier tube (PMT) 622 and an optical component loading module. The photomultiplier tube 622 is arranged within the optical component loading module. The optical component loading module of this embodiment of the present invention mainly comprises a shell body 631, a bottom cover 618, a first photoelectric control element 619, a second photoelectric control element 620, a base 621, a washer (gasket) 630, a light filter 629, a lens fixture 628, a lens 627, a lens fastener 626, a light-tight control component 624, a second light-tight component 625 and at least one actuator 623.

The bottom cover 618 is arranged on the bottom of the shell body 631. The first photoelectric control element 619 and the second photoelectric control element 620 are arranged within the shell body 631. The base 621 is arranged on the second photoelectric control element 620, and the photomultiplier tube 622 is arranged on the base 621. In this embodiment, the first photoelectric control element 619 and the second photoelectric control element 620 are mainly used to process photoelectric conversion signal of the photomultiplier tube 622.

The washer 630 is connected to the photomultiplier tube 622, and the filter 629 is connected with the washer 630. In this embodiment, the washer 630 is mainly used to prevent vibration from external or internal parts. The filter 629 is used to filter stray light free of disturbing. As for the lens fixture 628, it is arranged on the filter 629, and the lens 627 is fixed on the lens fixture 628. In addition, a lens fastener 626 is arranged on the upper outer edge of the lens 627. In this embodiment, the lens 627 mainly converges the light emitted by the reactants to the photomultiplier tube 622. The lens fastener 626 is used to stabilize the position of the lens 627, and the lens fixture 628 is used in conjunction with the lens fastener 626 to stabilize and tighten the lens 627.

As for the light-tight control component 624, it covers the outside of the lens 627. In addition, the second light-tight control component 625 covers the outside of the light-tight control component 624. Finally, at least one actuator 623 is connected to the light-tight control component 624. In this embodiment, the at least one actuator 623 may be an electromagnetic push-pull actuator for controlling the light-tight control component 624 to achieve the detection accuracy of lifting and lowering detection while light-tight is maintained without being disturbed by ambient light. Therefore, in this present embodiment, the best detection environment is achieved through co-operation of the first light-tight member 6063, the light-tight control component 624 and the second light-tight member 625 arranged on the light-tight cover 604. Therefore, the light detection device 603 can accurately detect the optical signal in the detection disk D without being disturbed by ambient light to judge the detection results.

Figure 10:
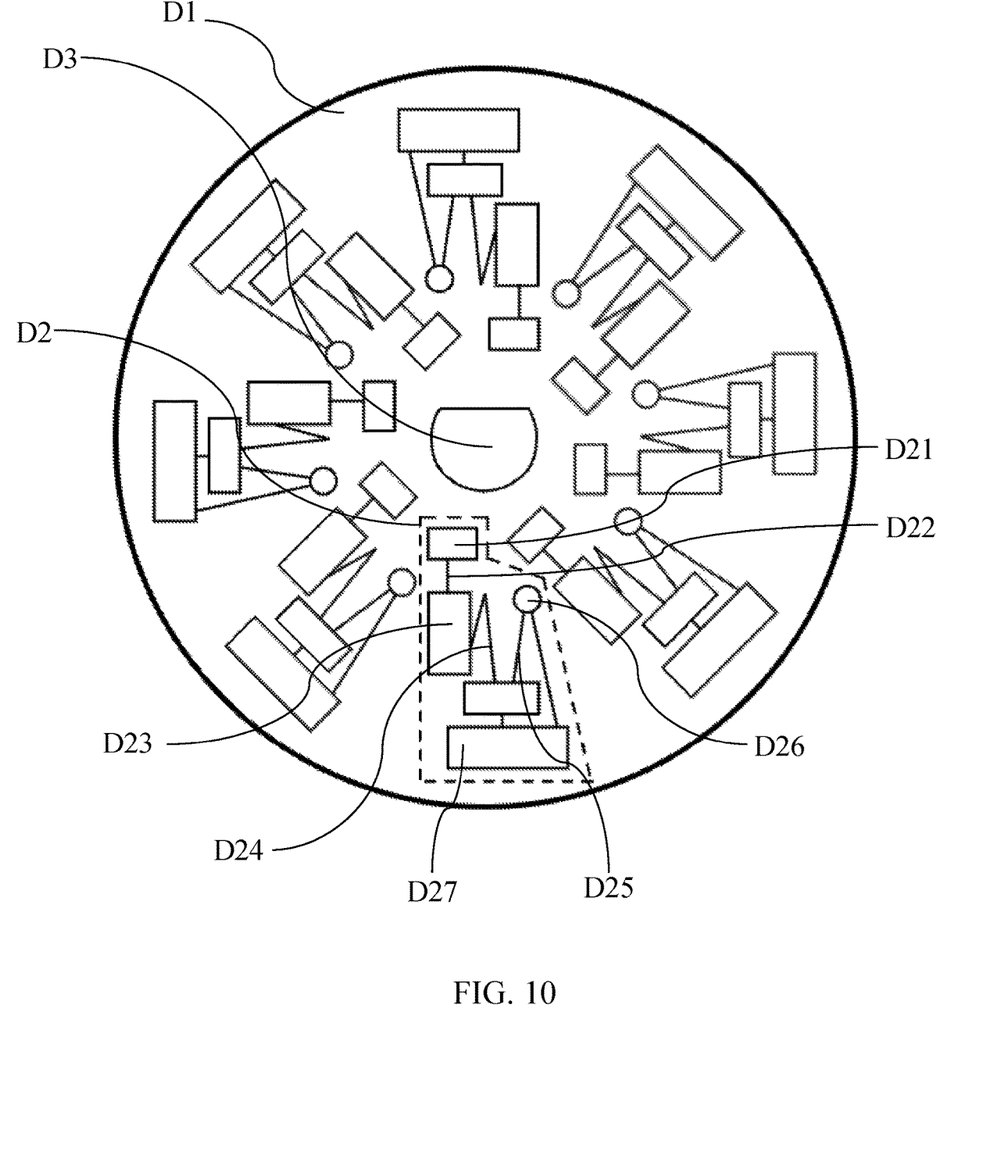
FIG. 10 illustrates a structural diagram of the detection disc in accordance with one embodiment of the invention.

Referring to FIG. 10, it illustrates a structural diagram of the detection disc in accordance with the embodiment of the invention. The invention can be used to detect a considerable number of detection discs D with different configurations, and the detection disc D in FIG. 10 is one example of the available implementations.

As shown in FIG. 10, the detection disc D of this embodiment includes a main body D1 and a plurality of detection units D2. A plurality of detection units D2 are arranged on the main body D1, and each detection unit D2 includes at least one sampling hole D21, a first channel D22, a detection tank D23, a siphon valve D24, a second channel D25, a vent hole (exhaust hole) D26, and a waste liquid tank D27. The first channel D22 is connected to the at least one sampling hole D21. The number of the at least one sampling hole D21 of this embodiment is 3, and they are converged to connect with the first channel D22. The detection tank D23 is connected with the first channel D22, and the siphon valve D24 is connected with the detection tank D23. The second channel D25 is connected with the siphon valve D24, and the second channel D25 is provided with a vent hole D26. Finally, the waste tank D27 is connected to the second channel D25.

As an example of the detection disc D in the embodiment of FIG. 10, the detection disc D in the embodiment of FIG. 10 can detect twelve biological samples because it includes twelve detection units D2. After filling 0, 5, 20, 100, 500, 2500, 5500 IU samples into each sampling hole D21 of the twelve detection units D2, magnetic bead antibodies and enzyme-labeled antibodies are sequentially filled into two sampling holes D21.

In this embodiment, the volume of the filled magnetic beads antibodies is between 1 to 100 microliters, preferred 20 microliters. The volume of the enzyme-labeled antibodies is between 1 to 100 microliter, preferred 20 microliters. Then, the second electrical machine 201 is activated at the first speed, and the reagent is centrifuged into the detection tank D23 to be incubated for 15 minutes. After incubated, the detection rotatable module 601 moves a base magnet (not shown) to the detection position, and the magnetic field is introduced at the detection tank D23 to adsorb the magnetic beads antibodies on the detection tank D23. Then, a sufficient amount of washing solution is poured into the sampling hole D21 above the detection tank D23, followed by rotating through the second electrical machine 201. The rotational speed is second RPM (Revolutions Per Minute). After the washing solution is entering into the detection tank D23, the detection rotatable module 601 is switched forward and backward oscillation to make the magnetic beads antibodies clean evenly. In the embodiment, the first rotational speed is less than second rotational speed, and the unit is RPM (Revolutions Per Minute).

The magnetic beads stacked at the bottom of the detection disc D are adsorbed on the top of the detection tank D23 by using the upper magnetic field for evenly washing, and the magnetic beads can be mixed evenly after vibration. Here, it can be known that magnets are arranged into the inner surface of light-tight cover 604 to achieve a critical function. Finally, the upper magnetic field is removed and the magnetic bead antibody is absorbed by the lower magnetic field, and the liquid is centrifuged into the waste liquid tank by adding the washing solution. The washing process is repeated twice, then performing the next detection step. Finally, the substrate is added through the sampling hole D21 to create chemiluminescence reaction with the reacted magnetic beads antibodies in the detection tank D23. Then, the light signal is detected by the light detection device 603.

Figure 11:
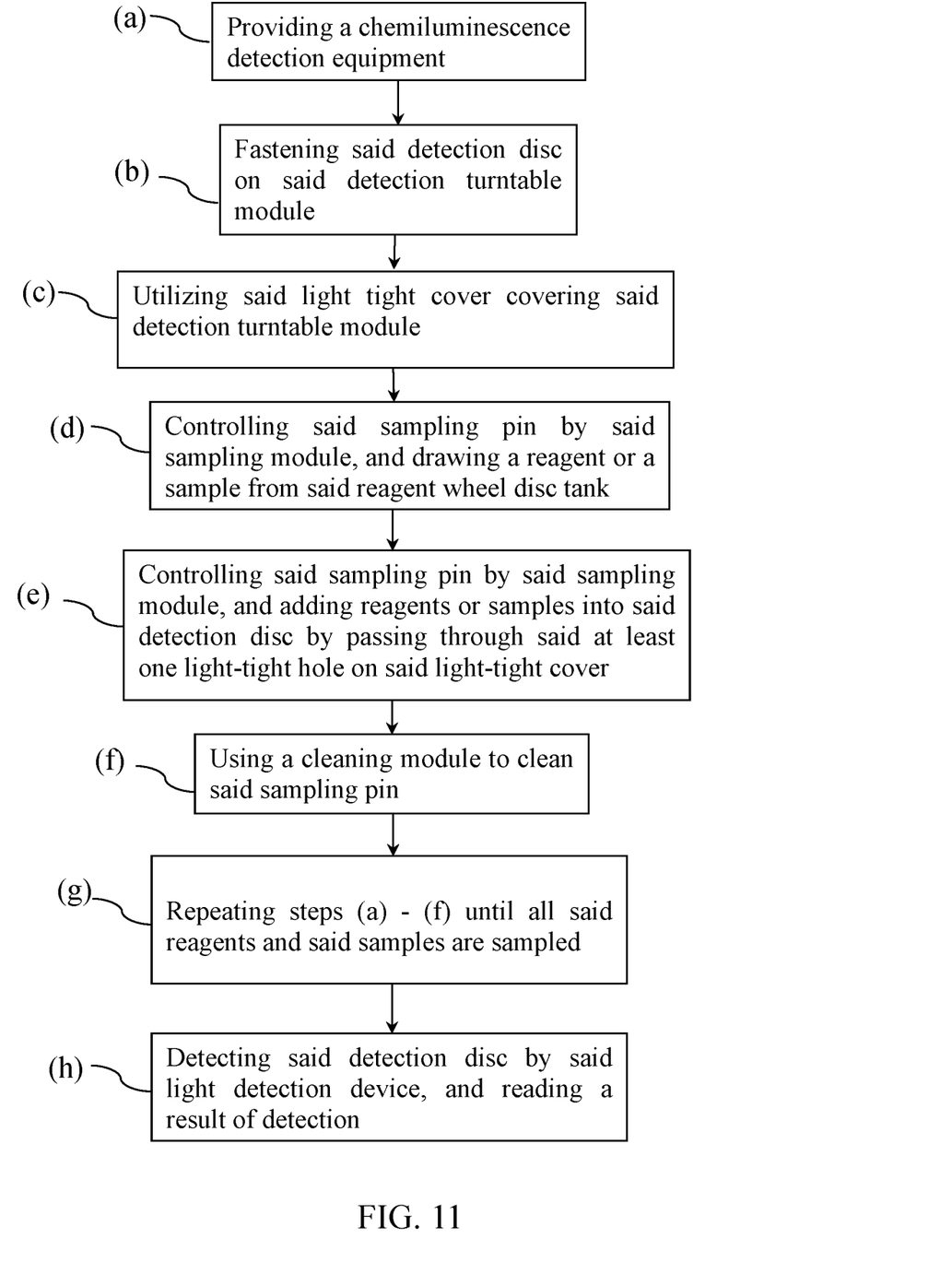
FIG. 11 illustrates a flow chart of the operation method of one embodiment of the invention.

Finally, referring to FIG. 11, it illustrates a flow chart of the operation method of one embodiment of the invention. As shown in FIG. 11, first, the step (a) provides the chemiluminescence detection equipment 10. Next, the step (b) performs fastening the detection disc D on a detection rotatable module 601. The next step (c) performs a light tight cover 604 covering the detection rotatable module 601. Then, the step (d) performs a sampling module 400 controlling a sampling pin 401, and a reagent or sample is drawn from a reagent wheel disc tank 300.

Next, the step (e) performs the sampling module 400 controlling the sampling pin 401, and the reagents or samples are added into the detection disc D by passing through at least one light-tight hole 6041 on the light-tight cover 604. Take the detection disk D in FIG. 10 for example, because the detection disk D in FIG. 10 has twelve detection units D2, a single reagent or sample can be added twelve times and cleaned when the detection is finished. For example, if there are twelve kinds of samples, washing process must be performed before adding samples among different samples. Therefore, when another reagent or sample is needed for sampling, the step (f) performs using a washing module 500 to clean the sampling pin 401.

Then, the step (g) repeats the steps (a)-(f) until all the reagents and samples are sampled. Finally, the step (h) detects the detection disc D by a light detection device 603, and reads the result of detection. In the step (c) above, the opening and closing angles of the light-tight cover 604 can be between 0 to 30 degrees, and the temperature of the reagent wheel disc tank 300 can be maintained at 15 degrees Celsius through a cooling device 301.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure. While the preferred embodiment of the invention has been illustrated and described, it will be appreciated that various changes can be made therein without departing from the spirit and scope of the invention.

What is claimed is:

1. A chemiluminescence detection equipment, comprising:
    a control module;
    a first electrical machine connected to said control module;
    a reagent wheel disc tank connected to said first electrical machine;
    a sampling module connected to said control module, wherein said sampling module includes a sampling pin;
    a washing module connected to said sampling module and said control module to clean said sampling pin;
    a second electrical machine connected to said control module;
    a detection module including:
    a detection rotatable module connected to said second electrical machine;
    a heating device connected to said control module and said detection rotatable module;
    a light detection device connected to said control module and said detection rotatable module; and
    a light tight cover to cover said detection rotatable module; and
    an electromagnetic valve connected to said control module;
    wherein said light-tight cover is provided with at least one light-tight hole, wherein each light-tight hole is opened and closed by said electromagnetic valve;
    wherein said electromagnetic valve is connected to a first sensor, and said light-tight cover is connected to a second sensor;
    wherein the first sensor is configured to confirm the operation of opening or closing the light-tight hole, and the second sensor is configured to confirm whether the light-tight cover is covered.

2. The equipment of claim 1, wherein said reagent wheel disc tank includes:
    a cooling device arranged on a bottom of said reagent wheel disc tank;
    a plurality of sample storage slots arranged on an outer ring of said reagent wheel disc tank;
    a substrate storage slot arranged on said outer ring of said reagent wheel disc tank; and
    a plurality of reagent storage slots arranged on an inner ring of said reagent wheel disc tank;
    wherein said plurality of reagent storage slots are arranged by a concentric circle, while said substrate storage slot and said sample storage slots are arranged by said concentric circle.

3. The equipment of claim 2, wherein said first electrical machine is engaged with said reagent wheel disc tank through a gear set.

4. The equipment of claim 3, wherein said gear set includes a first gear connected to said first electrical machine, and a plurality of second gears connected to said reagent storage slots, said plurality of second gears is configured on a bottom of said plurality of reagent storage slots.

5. The equipment of claim 1, wherein said sampling module comprises:
   a sampling arm connected to said sampling pin;
   a driving component connected to said sampling arm;
   a third electrical machine connected to said driving component; and
   a fourth electrical machine connected to said driving component;
   wherein said third electrical machine controls a transverse movement of said sampling arm, and said fourth electrical machine controls a longitudinal movement of said sampling arm, wherein said transverse movement and said longitudinal movement are in an identical plane.

6. The equipment of claim 1, wherein said sampling pin is connected to a resistance sensor.

7. The equipment of claim 1, wherein said light-tight cover is provided with a lock fastener.

8. The equipment of claim 1, wherein said detection rotatable module is connected with a detection disc.

9. The equipment of claim 8, wherein said detection rotatable module is provided with a fastener to control tightness of connection with said detection disc.

10. The equipment of claim 8, wherein said detection disc includes a main body and a plurality of detection units, each of said plurality of detection units includes:
    at least one sampling hole;
    a first channel connected to said at least one sampling hole;
    a detection tank connected with said first channel;
    a siphon valve connected with said detection tank;
    a second channel connected with said siphon valve, and wherein second channel is provided with a vent hole; and
    a waste liquid tank connected to said second channel.

11. The equipment of claim 1, wherein said light detection device comprises an optical component loading module and a photomultiplier tube (PMT) arranged within said optical component loading module.

12. The equipment of claim 11, wherein said optical component loading module comprises:
    a shell body;
    a bottom cover arranged on a bottom of said shell body;
    a first photoelectric control element arranged within said shell body;
    a second photoelectric control element arranged within said shell body;
    a base arranged on said second photoelectric control element, and wherein said photomultiplier tube is arranged on said base;
    a washer connected to said photomultiplier tube;
    a light filter connected with said washer;
    a lens fixture arranged on said light filter;
    a lens fixed on said lens fixture;
    a lens fastener arranged on an upper outer edge of said lens;
    a light-tight control component covered an outside of said lens;
    a second light-tight component covered an outside of said light-tight control component; and
    at least one actuator connected to said light-tight control component.

13. An operating method of a chemiluminescence detection equipment, comprising:
    (a) providing said chemiluminescence detection equipment according to claim 1;
    (b) fastening said detection disc on said detection rotatable module;
    (c) utilizing said light tight cover covering said detection rotatable module;
    (d) controlling said sampling pin by said sampling module, and drawing a reagent or a sample from said reagent wheel disc tank;
    (e) controlling said sampling pin by said sampling module, and adding reagents or samples into said detection disc by passing through said at least one light-tight hole on said light-tight cover;
    (f) using a washing module to clean said sampling pin; and
    (g) repeating said steps (a)-(f) until all said reagents and said samples are sampled; and
    (h) detecting said detection disc by said light detection device, and reading a result of detection.

* * * * *